(12) United States Patent
Rangarajan et al.

(10) Patent No.: US 6,583,871 B1
(45) Date of Patent: Jun. 24, 2003

(54) SYSTEM AND METHOD TO MEASURE CLOSED AREA DEFECTS

(75) Inventors: Bharath Rangarajan, Santa Clara, CA (US); Bhanwar Singh, Morgan Hill, CA (US); Khoi A. Phan, San Jose, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/911,238

(22) Filed: Jul. 23, 2001

(51) Int. Cl.[7] .............................................. G01N 21/00
(52) U.S. Cl. .............................. 356/237.5; 356/237.2; 356/237.4; 356/237.3
(58) Field of Search ...................... 356/237.2, 237.4, 356/237.5, 237.1, 237.3, 237.6

(56) References Cited

U.S. PATENT DOCUMENTS

| | | | | |
|---|---|---|---|---|
| 5,774,222 A | * | 6/1998 | Maeda et al. ............... 356/394 |
| 5,923,432 A | * | 7/1999 | Sawatari et al. ............. 356/349 |
| 6,081,325 A | * | 6/2000 | Leslie et al. .............. 356/237.2 |
| 6,292,260 B1 | * | 9/2001 | Lin et al. ................. 356/237.4 |
| 2002/0140930 A1 | * | 10/2002 | Lin et al. ................. 356/237.2 |

* cited by examiner

*Primary Examiner*—Hung Xuan Dang
*Assistant Examiner*—Tuyen Tra
(74) *Attorney, Agent, or Firm*—Amin & Turocy, LLP

(57) ABSTRACT

A system adapted to provide in-situ detection of closed area defects and a method for the same is provided. The system comprises a light source for directing light on to a wafer having a grating pattern etched thereon; a light detector for collecting the light reflected from the wafer; a processor operatively coupled to the light detector for converting the collected light into data associated with the grating pattern and determining the presence of the closed area defect; and a controller operatively coupled to the processor for determining whether the wafer requires additional processing to repair the closed area defect.

29 Claims, 12 Drawing Sheets

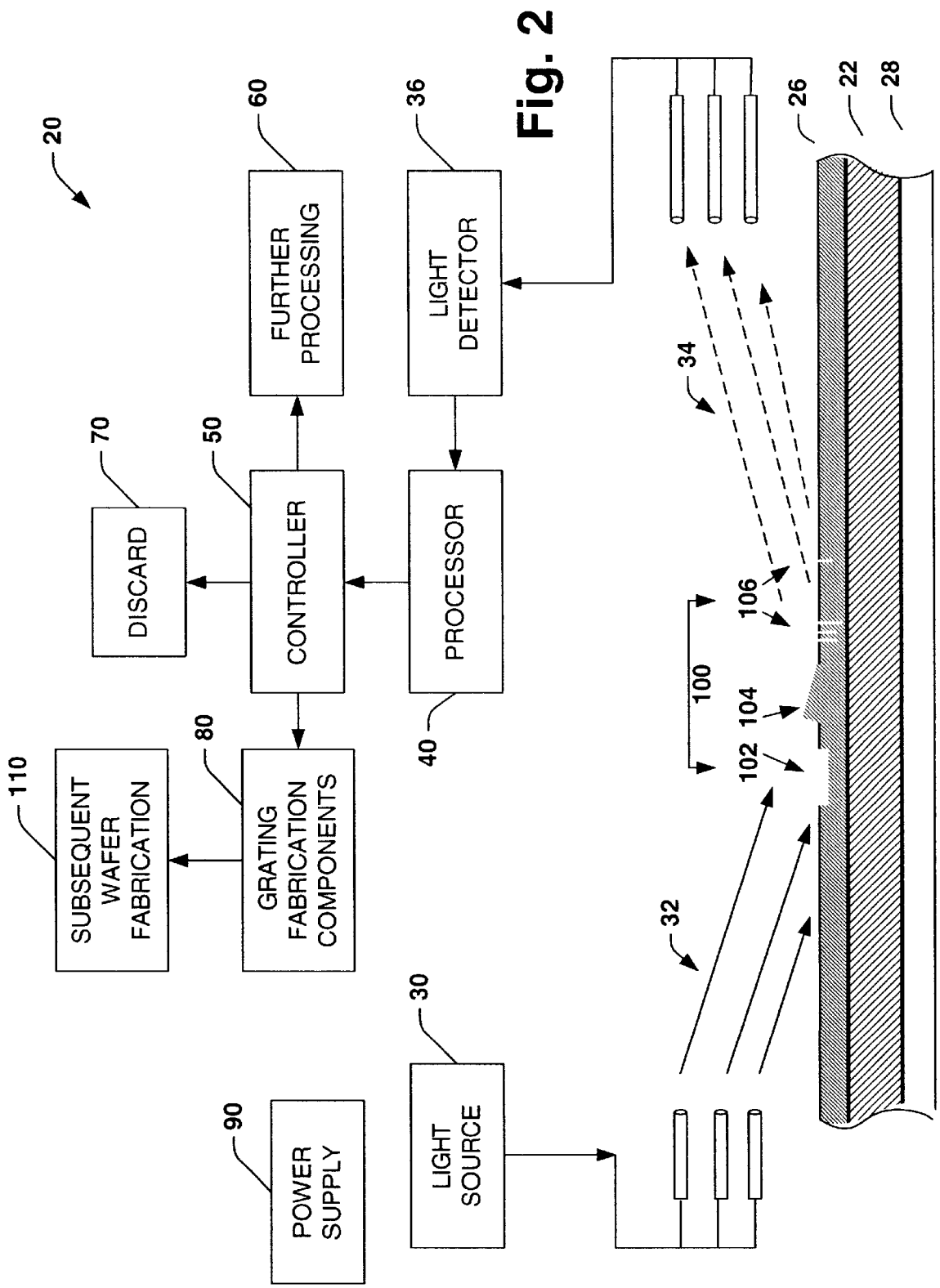

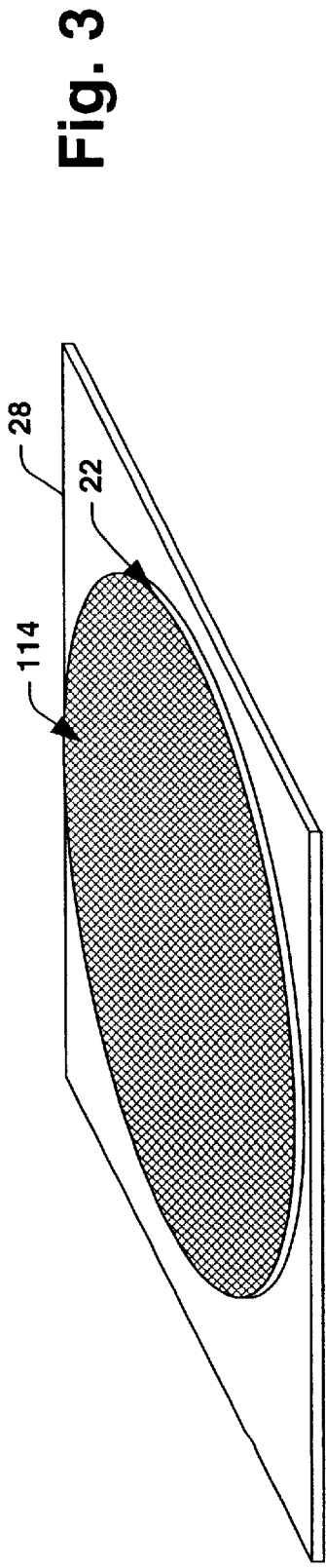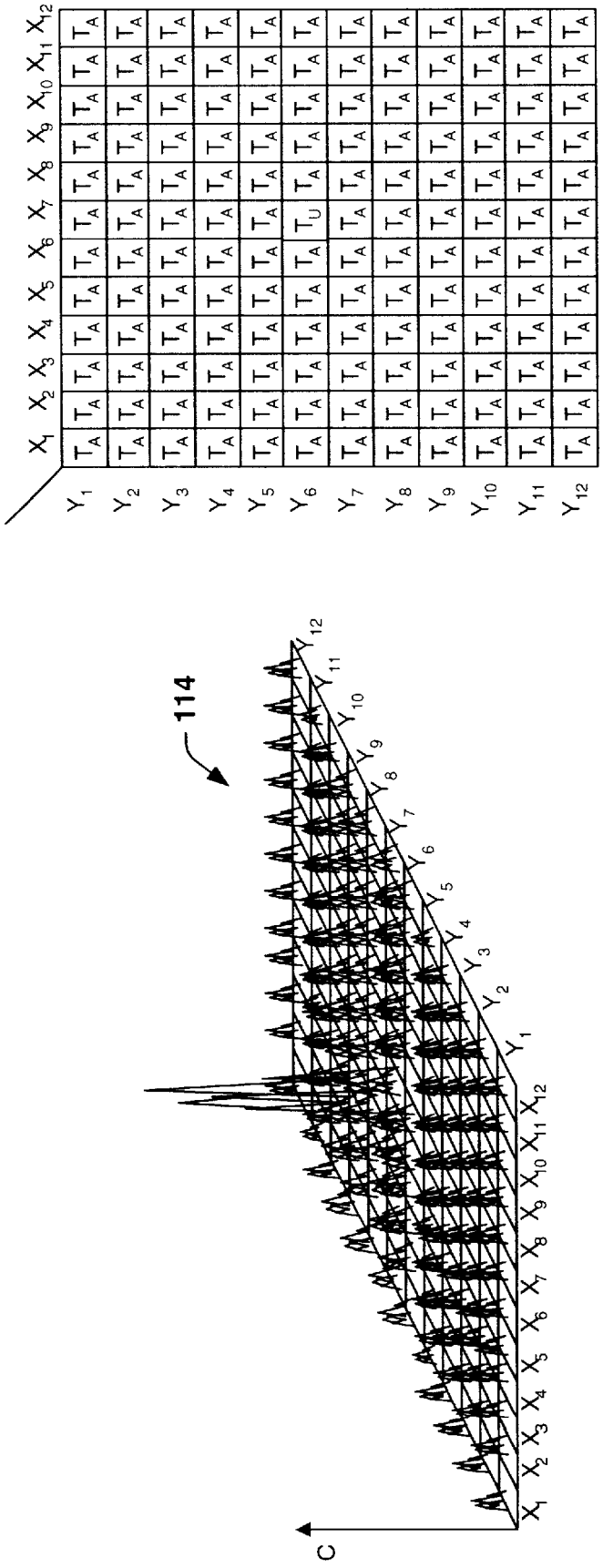

SYSTEM AND METHOD TO MEASURE CLOSED AREA DEFECTS

TECHNICAL FIELD

The present invention generally relates to semiconductor processing, and in particular to a system and method adapted to provide in-situ detection and reduction of closed area defects.

BACKGROUND

In the semiconductor industry there is a continuing trend toward higher device densities. To achieve these high densities there have been, and continue to be, efforts toward scaling down device dimensions (e.g., at sub-micron levels) on semiconductor wafers. In order to accomplish such high device packing densities, smaller feature sizes and more precise feature shapes are required. This may include the width and spacing of interconnecting lines, spacing and diameter of contact holes, and the surface geometry, such as corners and edges, of various features. Achieving smaller dimensions depends, at least in part, on the ability to accurately reproduce mask features on a wafer. For example, if edges are not developed as edges, or if lines have intrusions or extrusions, then the pattern may not produce the desired electrical conductive and/or insulating properties. Thus, a system and method for detecting when defects have been developed on a wafer is required.

The process of manufacturing semiconductors, or integrated circuits (commonly called ICs, or chips), typically involves photolithography which may consist of more than a hundred acts, during which hundreds of copies of an integrated circuit may be formed on a single wafer. In general, lithography refers to processes for pattern transfer between various media. It is a technique used for integrated circuit fabrication in which a silicon slice, the wafer, is coated uniformly with a radiation-sensitive film, the photoresist. The photoresist coated substrate is baked to evaporate any solvent in the photoresist composition and to fix the photoresist coating onto the substrate. The baked coated surface of the substrate is next subjected to selective radiation using a mask; that is, a mask is employed to effect an image-wise exposure to radiation. The mask permits radiation to contact certain areas of the photoresist and prevents radiation from contacting other areas of the photoresist. This selective radiation exposure causes a chemical transformation in the exposed areas of the photoresist coated surface. Types of radiation commonly used in microlithographic processes include visible light, ultraviolet (UV) light and electron beam radiant energy. After selective exposure, the photoresist coated substrate is treated with a developer solution to dissolve and remove either the radiation-exposed or the unexposed areas of the photoresist (depending upon whether a positive photoresist or a negative photoresist is utilized) resulting in a patterned or developed photoresist.

The process may be repeated a number of times depending on the desired number of layers and features to be formed. The layering process creates electrically active regions in and on the semiconductor wafer surface. If the patterns are not substantially accurately reproduced on the wafer surface, then the electrically active regions may not perform as desired, leading to an overall degradation of chip performance. In particular, closed area defects such as malformed or undeveloped edges, corners and lines as well as undesired depressions, dimples, protrusions and pinholes in the layers may adversely affect the performance of the semiconductor. Adverse effects may include increased resistance, decreased capacitance, ineffective insulation between layers and features, and poor conductivity and interconnections between layers and features.

Conventional methods for detection and reduction of closed area defects have been ineffective in mitigating closed area defect problems and associated yield losses and costs for many reasons. For example, conventional methods rely on pre-set timed check points to monitor and detect for the presence of defects on a wafer as opposed to allowing the detection system to operate in a continuous manner on the fabrication line. In addition, conventional methods and systems do not provide for in-situ detection and feedback control. Feedback control and in-situ detection systems/methods provide current data and other pertinent information to the fabrication system rather than gathering this information at or near the end of the fabrication process. In addition, such in-line feedback methods/systems decrease yield loss, fabrication costs and produce less waste as fewer wafers are discarded and more wafers having closed area defects are processed further to reduce the defects. Furthermore, such methods facilitate mitigating recurrence of closed area defects on subsequent wafers.

Thus, an in-line system and method to detect and mitigate closed area defects in semiconductor wafers are desired to increase overall semiconductor quality and performance.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description presented later.

The present invention provides a system and a method for in-situ detection and reduction of closed area defects in wafers having a grating pattern etched thereon. The present invention facilitates controlling quality and mitigating yield loss in semiconductor fabrication by signaling to the fabrication system (and to a user) that a subject wafer contains closed area defects of a determined magnitude and thus requires additional processing to reduce the defects. In addition, the present invention involves regulating the fabrication process using run-time feedback, which facilitates detection and reduction of closed area defects on subsequently fabricated wafers. The run-time feedback or feedback control permits data related to detected closed area defects to be communicated back to fabrication components. In response to the data, the fabrication components make adjustments accordingly so as to mitigate subsequent occurrences of closed area defects on the grating patterns and on the wafer in general.

As a result, the present invention provides improved semiconductor fabrication as compared to conventional systems by facilitating the achievement of smaller feature sizes and higher packing densities while mitigating yield loss and the occurrence of closed area defects in subsequent wafers.

An exemplary system for in-situ detection and reduction of closed area defects on a wafer may employ one or more light sources arranged to project light onto a grating pattern developed on a wafer and one or more light detecting devices (e.g. photo detector, photodiode) for detecting light signatures reflected by the grating. The light signature reflected from the grating (and wafer) is characteristic of the presence (or absence) of losed area defects (e.g. intrusion defects, extrusion defects, corner defects, pinhole defects.

A processor receives the reflected light signature from the light detector and processes it by converting or interpreting the reflected light into an associated data form, such as numerical or graphical data, in order to determine the presence of closed area defects. The processor may also determine a quantity or level of defects present using the reflected light signature. Determining the presence and level of closed area defects is performed by comparing the data associated with the reflected light signature (subject grating pattern) with known light signatures in connection with known grating patterns.

In addition, the processor may compare the actual level of detected closed area defects to a threshold level of closed area defects to determine whether enough closed area defects are present to constitute "a positive detection". Information produced and assimilated by the processor is then communicated to a controller for determining whether the wafer requires additional processing. The controller may signal the fabrication system (and a user) that additional processing of the subject wafer is needed to repair the detected closed area defects. Alternatively, the controller may signal the subject wafer to be discarded due to an unacceptable level of closed area defects detected. Detecting and mitigating the occurrence of closed area defects on grating patterns on the wafer are critical to the chip manufacturing process due to the detrimental effects closed area defects have on feature and layer isolation. These detrimental effects adversely influence conducting and insulating properties as well. Detection and mitigation of closed area defects also facilitates producing semiconductors that exhibit consistency in both chip quality and feature performance.

In accordance with one aspect of the present invention, a system adapted to provide in-situ detection of closed area defects is provided. A light source directs light on to a wafer having a grating pattern etched thereon. A light detector collects the light reflected from the wafer, and a processor operatively coupled to the light detector converts the collected light into data associated with the grating pattern and determines the presence of the closed area defect. A controller operatively coupled to the processor determines whether the wafer requires additional processing to repair the closed area defect.

Another aspect of the invention provides a system adapted to provide in-situ detection and mitigation of closed area defects. One or more grating fabrication components creates a grating pattern on a wafer. A light source directs light on to the wafer having the grating pattern etched thereon. A light detector collects the light reflected from the wafer, and a processor operatively coupled to the light detector converts the collected light into data associated with the grating pattern and determines the presence of the closed area defect. A first controller operatively coupled to the processor determines whether the wafer requires additional processing to repair the closed area defect. A second controller operatively coupled to the processor communicates adjustments to the one or more grating fabrication components in order to mitigate subsequent occurrences of closed area defects.

Yet another aspect of the present invention provides a method for detection and reduction of closed area defects on a wafer. Light is directed at the wafer having a grating patterned etched thereon. A light signature reflected from the wafer is collected. The presence of closed area defects on the wafer is detected; and if the closed area defects are detected, then proceeding to additional processing of the wafer to reduce the closed area defects.

Still another aspect of the present invention provides a method for detection and reduction of closed area defects on a wafer. The method comprises: patterning a grating onto the wafer using one or more grating fabrication components; directing a light at the wafer having the grating patterned etched thereon; collecting a light signature reflected from the wafer; detecting for the presence of the closed area defects on the wafer; if the closed area defects are detected, then performing additional processing to reduce the closed area defects; and if the closed area defects are detected, then communicating determined adjustments to the one or more grating fabrication components.

Yet another aspect of the preset invention provides a system a system for detection and reduction of closed area defects on a wafer comprising: means for directing a light at the wafer having a grating patterned etched thereon; means for collecting a light signature reflected from the wafer; means for detecting for the presence of the closed area defects on the wafer; and if the closed area defects are detected, then means for signaling the wafer to proceed to additional processing to reduce the closed area defects.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The present invention is illustrated by way of example in the accompanying figures in which:

FIG. 2 is a schematic partial block diagram of an in-situ (in-line) system in accordance with an aspect of the present invention;

FIG. 3 is a perspective illustration of a wafer that may be fabricated in accordance with an aspect of the present invention;

FIG. 4 is a representative three-dimensional grid map of a wafer illustrating signature measurements taken at grid blocks of the wafer in accordance with an aspect of the present invention;

FIG. 5 is a signature measurement table correlating the measurements of FIG. 4 with desired values for the measurements in accordance with the present invention;

DETAILED DESCRIPTION

Figure 1:
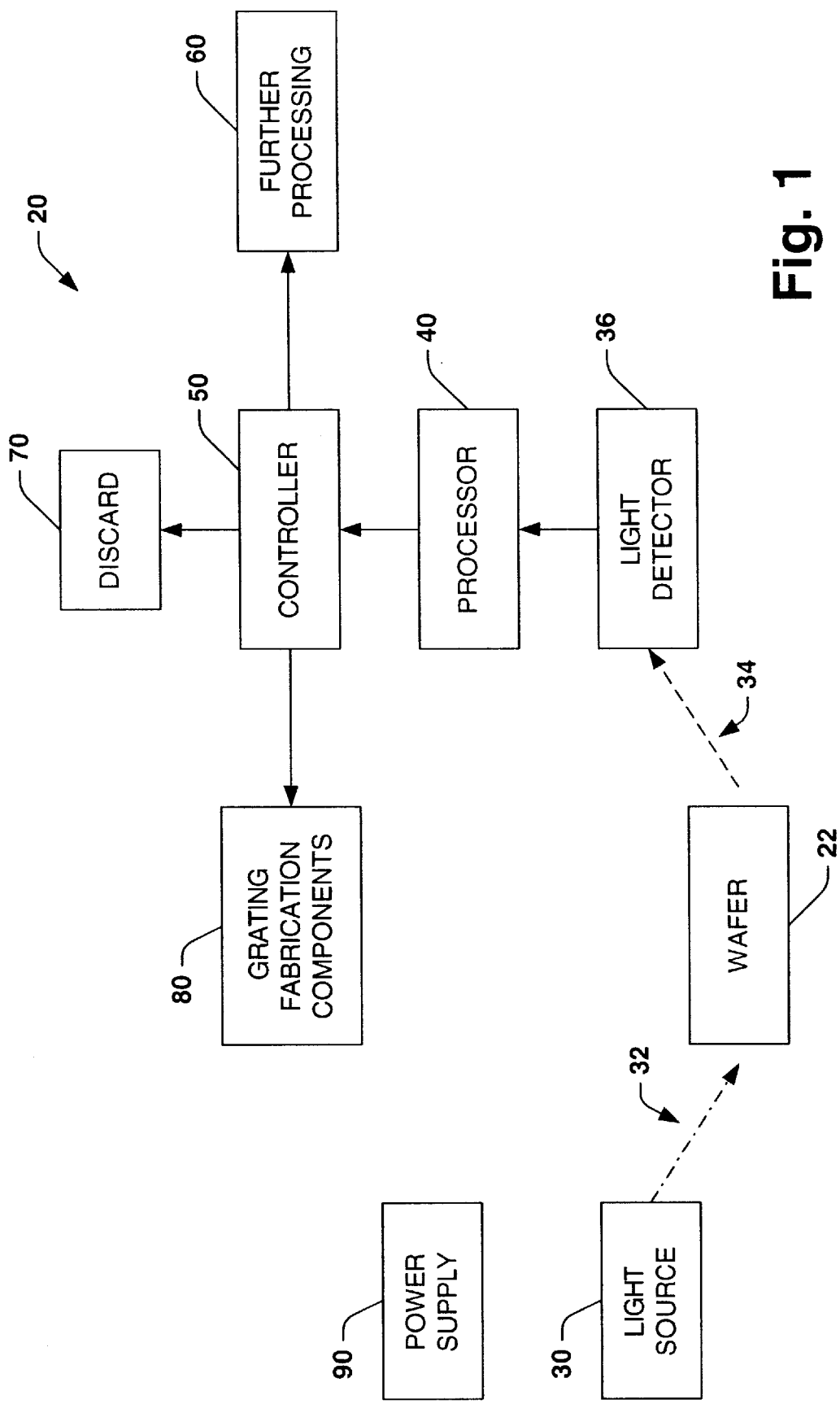
FIG. 1 is a schematic block diagram of an in-situ (in-line) system in accordance with one aspect of the present invention.

The present invention will now be described with reference to the drawings, wherein like reference numerals are used to refer to like elements throughout. The following detailed description is of the best modes presently contemplated by the inventors for practicing the invention. It should be understood that the description of these aspects are merely illustrative and that they should not be taken in a limiting sense.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed. Furthermore, as used in this application, the term "component" is intended to refer to a computer-related entity, either hardware, a combination of hardware and software, software, or software in execution. For example, a component may be, but is not limited to being, a process running on a processor, a processor, an object, an executable, a thread of execution, a program, and a computer. By way of illustration, both an application running on a server and the server can be a component.

Referring initially to FIG. 1, a schematic block diagram of a system 20 adapted to provide in-situ detection and reduction of closed area defects formed on a wafer 22 is shown in accordance with one aspect of the present invention. The wafer 22 includes a grating pattern (not shown) in which the occurrence of closed area defects is fairly common. It should be understood that the wafer 22 may include one or more grating patterns formed thereon. For the sake of brevity, the wafer 22 having one or more grating patterns is referred to as the wafer 22 in the present invention.

A light source 30 directs an incident beam of light 32 at the wafer 22. The light source 30 may comprise of one or more or a series of light sources directed at the wafer 22. Examples of light sources contemplated by the present invention include, but are not limited to, a laser such as a laser diode or a helium neon gas laser.

Light reflected 34 from the wafer 22 is collected by a light detector 36. The reflected light 34 may also be a reflected light signature associated with the wafer 22. The light detector 36 comprises one or more light detecting devices and collects light in accordance with conventional scatterometry techniques. Examples of light detectors include photo diodes and photo detectors.

It should be appreciated that reference to the wafer 22 refers to the wafer 22 having a grating pattern etched thereon. It should also be appreciated that the incident light 32 may also pass through the wafer 22 and then may be collected using the light detector 36 as previously described.

The reflected light 34 (reflected light signature) is communicated to a processor 40, which is operatively coupled to the light detector 36. The processor 40 interprets or converts the reflected light 34 into a data form which is associated with the wafer 22 as well as the grating pattern present thereon. Examples of data forms include numerical data and graphical data.

The processor 40 may be any of a plurality of processors, such as the AMD K7, and/or other similar and compatible processors. The manner in which the processor 40 can be programmed to carry out the functions relating to the present invention will be readily apparent to those having ordinary skill in the art based on the description provided herein. The processor 40 comprises a conventional scatterometry system (FIG. 6) and performs the interpretation and/or conversion of the reflected light 34 using such scatterometry system and related scatterometry techniques.

The processor 40 determines the presence of closed area defects on the wafer 22 by comparing the data associated with the grating pattern to a database comprising known grating patterns (not shown). The database as well as the data associated with the wafer 22 may be stored in a memory (not shown), which is connected to and accessible to the processor 40.

Alternatively or in addition, the processor 40 determines a level of closed area defects which is present on the wafer 22 by comparing the data associated with the grating pattern to the database. By determining the level or a quantitative amount of closed area defects present in the grating pattern, the processor 40 is able to provide other parts of the system 20 with more precise information relating to the characteristics of the wafer 22, thus facilitating a further determination in connection with an amount or types of further processing needed to reduce the presence of the closed area defects.

In addition, the processor 40 may be programmed to communicate the presence of the closed area defects if such closed area defects exist at a pre-determined threshold level. For example, a user may pre-determine and program the processor 40 to determine that closed area defects are deemed "present" if they exist on the wafer 22 at a level 3 or higher. That is, closed area defects present on the wafer 22 at a level of 2 or lower renders a "no closed area defects present" determination from the processor 40. Each level corresponds to an amount or degree of closed area defects present/detected as is defined by the user.

After the processor 40 performs its described functions and makes its determinations as described above, the processor 40 communicates its findings to the controller 50. The controller 50 is operatively coupled to the processor 40. The controller 50 determines whether the wafer 22 requires additional processing 60 to repair and/or reduce detected closed area defects. Alternatively, or in addition, the controller 50 determines whether to discard 70 to the wafer 22 as a result of an unacceptable level of closed area defects. The controller 50 formulates its determination using the information received from the processor 40.

If the level of detected closed area defects falls within a pre-determined acceptable level range, then the controller 50 directs the wafer 22 for additional/further processing 60. If the level of detected closed area defects exceeds the level range, then the controller 50 directs the wafer 22 to be discarded 70 because the sheer amount of closed area defects has rendered the wafer 22 unsalvageable. The determination to discard 70 the wafer may also be done using a programmed cost-benefit analysis. That is, the cost of repairing or reducing the detected closed area defects on the wafer 22 outweighs the benefit received from such repair. Therefore, it would be more cost and time effective to simply discard the wafer 22.

Alternatively, or in addition, the controller 50 may also communicate adjustments to one or more grating fabrication components 80 for the purpose of mitigating occurrences of closed area defects in subsequent grating patterns in subsequent wafers. Examples of grating fabrication components include the conventional tools, developers, solutions, photo masks, post-etch bake conditions, irradiation methods, and exposure time involved in and associated with forming a grating pattern on the wafer 22.

The controller 50 may also be programmed using non-linear training systems (not shown) to determine the appropriate adjustments to make according to the information received from the processor 40. Because the processor 40 and the controller 50 function cooperatively, receiving and processing data corresponding to grating patterns as they are printed and developed on the wafer, the system 20 mitigates closed area defect formation as it is detected, and thus facilitates achieving higher quality semiconductors that exhibit greater consistency with respect to feature formation and performance.

The system 20 operates using any conventional power supply 90 suitable to carry out the present invention.

Turning now to FIG. 2, a schematic partial block diagram of the system 20 is shown in accordance with another aspect of the invention. The wafer 22 is shown having closed area defects 100 formed on the grating pattern 26. As shown, the wafer is supported by a chuck 28. Closed area defects 100 comprise an intrusion defect 102, an extrusion or protrusion defect 104 and pinhole defects 106. Closed area defects may also include corner defects (not shown). For ease of understanding, defects 102, 104 and 106 are referred to collectively as closed area defects 100.

Closed area defects 100 cause the light 34 to reflect in different, quantifiable ways. Therefore, each reflected light signature collected by the light detector 36 is unique and characteristic of the particular grating pattern and wafer subjected to the system 20. There is, however, the possibility that more than one wafer may have nearly identical reflected light signatures, but the occurrence of this does not adversely affect any aspect of the present invention described herein.

The light 34 reflected from (or passed through) the grating pattern 26 indicates that the closed area defects 100 are present on the grating pattern 26. As described in FIG. 1, the processor 40 converts or interprets the reflected light 34 into a data form using a conventional scatterometry system and related scatterometry techniques. Scatterometry systems are well known in the art, and therefore further discussion related thereto is limited for sake of brevity. Sample scatterometry systems are briefly described in association with FIG. 6. It is to be appreciated that any suitable scatterometry system may be employed to carry out the present invention and such systems are intended to fall within the scope of the claims appended hereto.

The processor 40 then determines whether closed area defects are present. According to the wafer 22 illustrated in FIG. 2, the processor 40 determines closed area defects 100 are present on the grating pattern 26. Information relating to the closed area defects 100 is communicated to the controller 50, where it is determined whether the wafer 22 should be directed to additional processing 60 or be discarded 70.

For either option 60 or option 70 chosen, the controller 50 signals the fabrication system to direct the wafer 22 in the determined direction. The signal may be in the form of an alarm such as an audible alarm. The signal may also be recorded in the fabrication system as having been activated along with other pertinent information relating to the cause of the signal. For example, information from the processor 40 and information further gathered by the controller 50 in connection with the wafer 22 and grating pattern 26 may also be recorded with the activated "signal" so that a user could manually evaluate both the fabrication and in-situ detection systems.

In addition to determining whether to discard or to direct the wafer on to further processing, the controller 50 is also determining the necessary adjustments to make to the grating fabrication components 80 so as to mitigate and reduce the occurrence of closed area defects 100 in subsequent wafers and grating patterns 110.

Furthermore, the controller 50 may be programmed to direct the wafer 22 to either additional processing or discard but not both. However, the controller 50 determines necessary adjustments to the grating fabrication components regardless of whether the wafer 22 is discarded or directed on to further processing. After the grating fabrication components 80 are adjusted, subsequent grating patterning and wafer fabrication continues.

According to the present invention, the semiconductor fabrication system does not need to stop for any substantial length of time in order to perform the methods described herewith the system 20. Therefore, grating patterning is continuously being optimized while the fabrication process progresses from cycle to cycle.

FIGS. 3–5 show yet another aspect of the present invention. The processor 40 may be programmed to partition the grating pattern (and wafer) into a coordinate grid comprising one or more grid blocks 114 ($X_1Y_1 \ldots X_{12}, Y_{12}$). In FIG. 3, the wafer 22 and grating pattern 26 is shown wherein the wafer 22 and grating pattern 26 are mapped into one or more grid blocks. Each grid block 114 (XY) corresponds to a particular portion of the grating pattern 26 and wafer 22. The data assimilated from the processor 40 provides more precise information relating to the almost exact (if not exact) location of the closed area defects 100. In particular, FIG. 4 illustrates that the closed area defects 100 are located at particular XY coordinate positions, which correspond to the grating pattern 26. The reflected light signatures for all the grid blocks 114 are also shown in FIG. 4. The signatures may be generated by light reflected from and/or passed through, the grating pattern 26 on the wafer 22.

The coordinate grid allows the system 20 to provide more precise detection and analysis of closed area defects 100 as they appear on the grating pattern 26. In fact, if a particular portion of grating patterns on more than one wafer is particularly prone to closed area defects, the processor 40 and controller 50 can be programmed to concentrate on that particular portion of the wafer. In fact, the processor 40 and/or controller 50 can facilitate determining particular areas on grating patterns on which closed area defects consistently form. The system 20 may then be programmed to concentrate on these pre-assessed problematic areas. It is to be appreciated that the wafer 22 may be partitioned into any suitable number of portions or grid blocks.

FIG. 5 illustrates a table of acceptable and unacceptable signatures. It can be seen that all the signatures are acceptable except a signature for grid $X_7Y_6$. The set of signatures depicted in FIG. 5 can be analyzed collectively as a master signature, can be analyzed in subsets to evaluate, for example, intermediate deposition and/or can be analyzed individually to determine whether an acceptable deposition condition exists. The analysis of the signatures is used by the processor 40 and the controller 50 to determine whether closed area defects exist and whether the wafer 22 should be directed on to further processing or be discarded, respectively, in light of the detected closed area defects.

Figure 6:
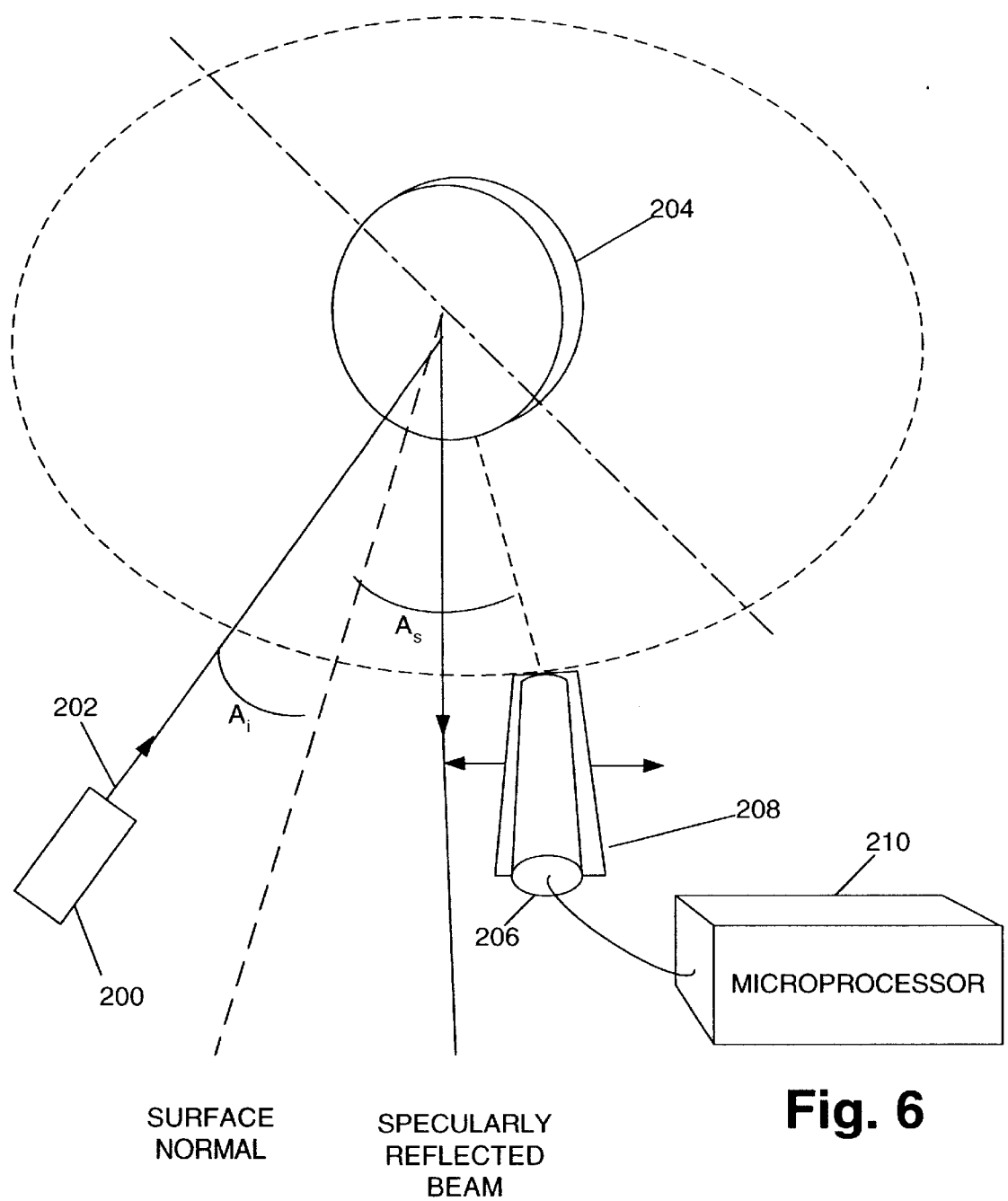
FIG. 6 illustrates an exemplary scatterometry system collecting reflected light in accordance with an aspect of the present invention.

FIG. 6 illustrates an exemplary scatterometry system collecting reflected light. Light from a laser 200 is brought to focus in any suitable well-known manner to form a beam 202. A sample, such as a wafer 204 is placed in the path of the beam 202 and a photo detector or photo multiplier 206 of any suitable well-known construction. Different detector methods may be employed to determine the scattered power. To obtain a grating pitch, the photo detector or photo multiplier 206 may be mounted on a rotation stage 208 of any suitable well-known design. A microprocessor 210, of any suitable well-known design, may be used to process detector readouts, including, but not limited to, angular locations of different diffracted orders leading to diffraction grating pitches being calculated. Thus, light reflected from the sample 204 may be accurately measured.

Figure 7:
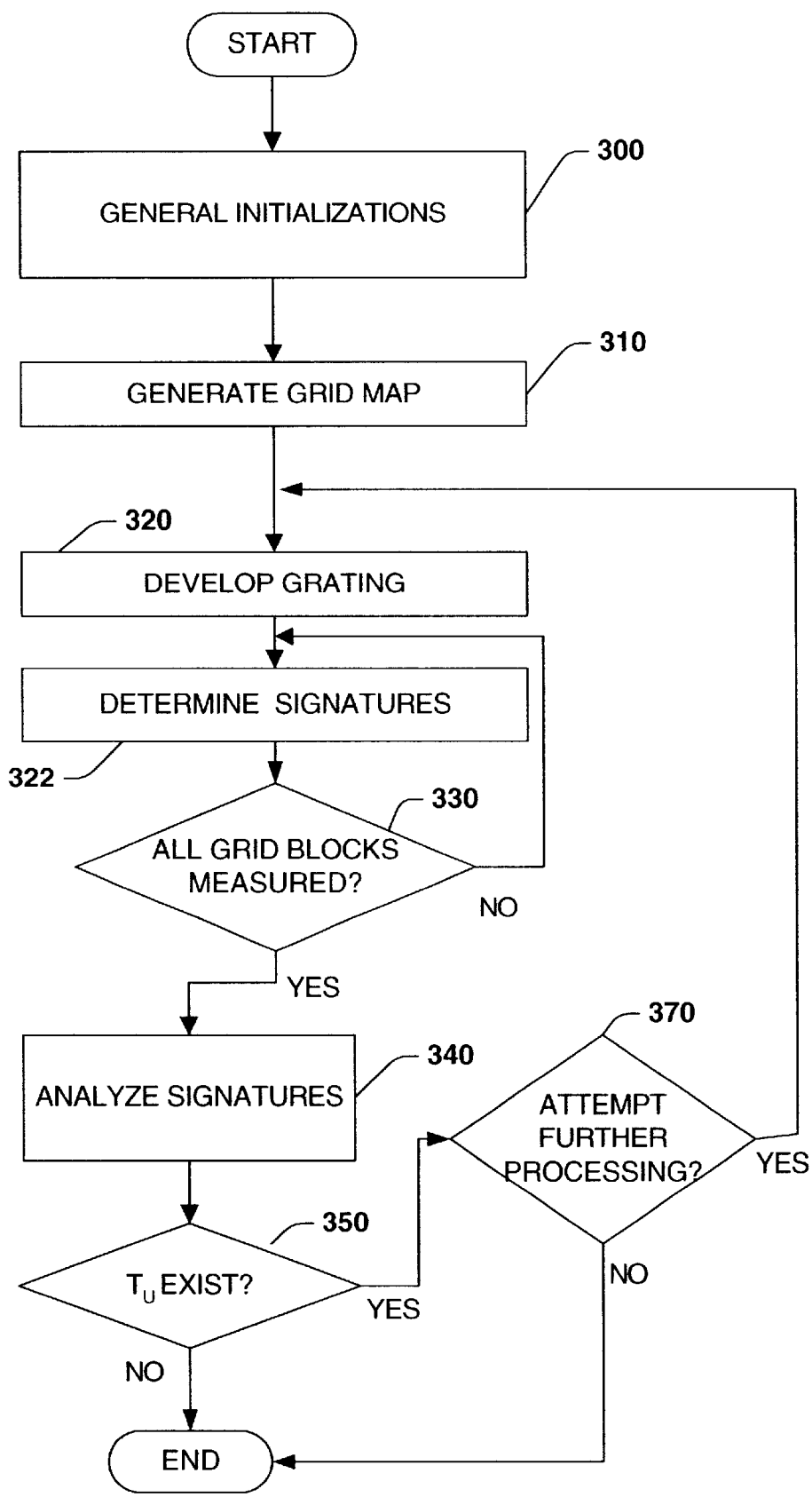
FIG. 7 is a flow diagram illustrating an example methodology for detecting and mitigating closed area defects in-line in accordance with an aspect of the present invention.
Figure 8:
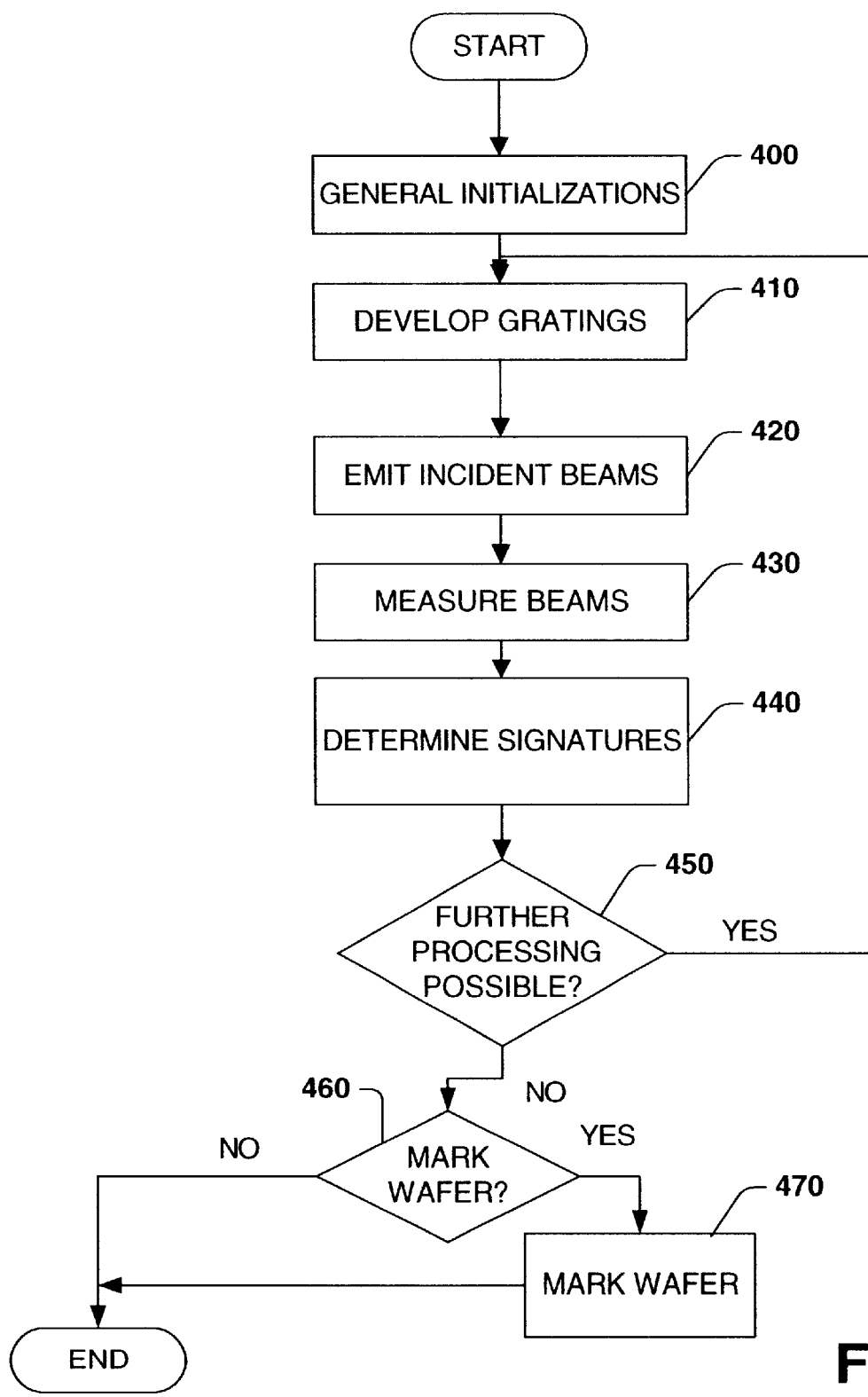
FIG. 8 is a flow diagram illustrating another example methodology for detecting and mitigating defects in-line in accordance with an aspect of the present invention.

In view of the exemplary systems shown and described above, a methodology, which may be implemented in accordance with the present invention, will be better appreciated with reference to the flow diagrams of FIGS. 7 and 8. While, for purposes of simplicity of explanation, the methodologies of FIG. 7 and FIG. 8 are shown and described as a series of acts. It is to be understood and appreciated that the present invention is not limited by the order of the acts, as some acts may, in accordance with the present invention, occur in different orders, and/or concurrently with other acts, from that shown and described herein. Moreover, not all illustrated acts may be required to implement a methodology in accordance with the present invention.

FIG. 7 is a flow diagram illustrating one particular methodology for carrying out the present invention. At 300, a processor performs general initializations to a system for monitoring defects. At 310, the processor maps at least a portion of a mask into a plurality of grid blocks "XY". At 320, the manufacturing process is begun. At 322, signature determinations are made with respect to the various wafer portions mapped by the respective grid blocks XY. At 330, the processor determines if all grid block signatures have been taken. If no, the processor returns to 322. If yes, then at 340 the processor analyzes the signature, or signatures, against a table of acceptable signatures. At 350, the processor determines if the signatures are acceptable. If the signatures are acceptable, the processor ends the iteration of the deposition process. If at 350 an unacceptable signature is found, the processor advances to 370 where a determination is made concerning whether further manufacturing will be undertaken. If no further processing is to be undertaken, then the wafer can be marked for further processing, and/or destruction, and alarms may be sent to subsequent methods, and/or apparatus, concerning the unacceptable defect condition, after which the manufacturing process concludes. If the determination at 370 is YES, then the present iteration is then ended and the process returns to 320 to perform another iteration.

FIG. 8 is a flow diagram illustrating another particular methodology for carrying out the present invention. At 400, general initializations and/or configurations are performed. At 410, manufacturing begins. At 420, incident light beams are emitted onto the wafer and at 430 the reflected, passed through and/or scattered beams are measured. At 440, the signatures from the wafer upon which the incident beams were directed are analyzed. At 450, a determination is made concerning whether processing is warranted. If the determination at 450 is YES, then manufacturing continues. If the determination at 450 is NO, then at 460 a determination is made concerning whether the wafer should be marked. If at 460 the determination is YES, then at 470 the wafer is marked for subsequent processing and/or destruction. Further, alarms and/or alerts may be set to inform subsequent apparatus and methods of the defect condition on the wafer. It is to be appreciated by one skilled in the art that while the acts in FIG. 8 are shown in a linear order, that emitting the incident beams, measuring the reflected, passed through and/or diffracted beams and determining whether the manufacturing process has produced a wafer an undesirable defect level may occur simultaneously, in situ.

Scatterometry is a technique for extracting information about a surface upon which an incident light has been directed. Information concerning properties including, but not limited to, dishing, erosion, profile, chemical composition, thickness of thin films and critical dimensions of features present on a surface such as a wafer can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N=n-jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 9:
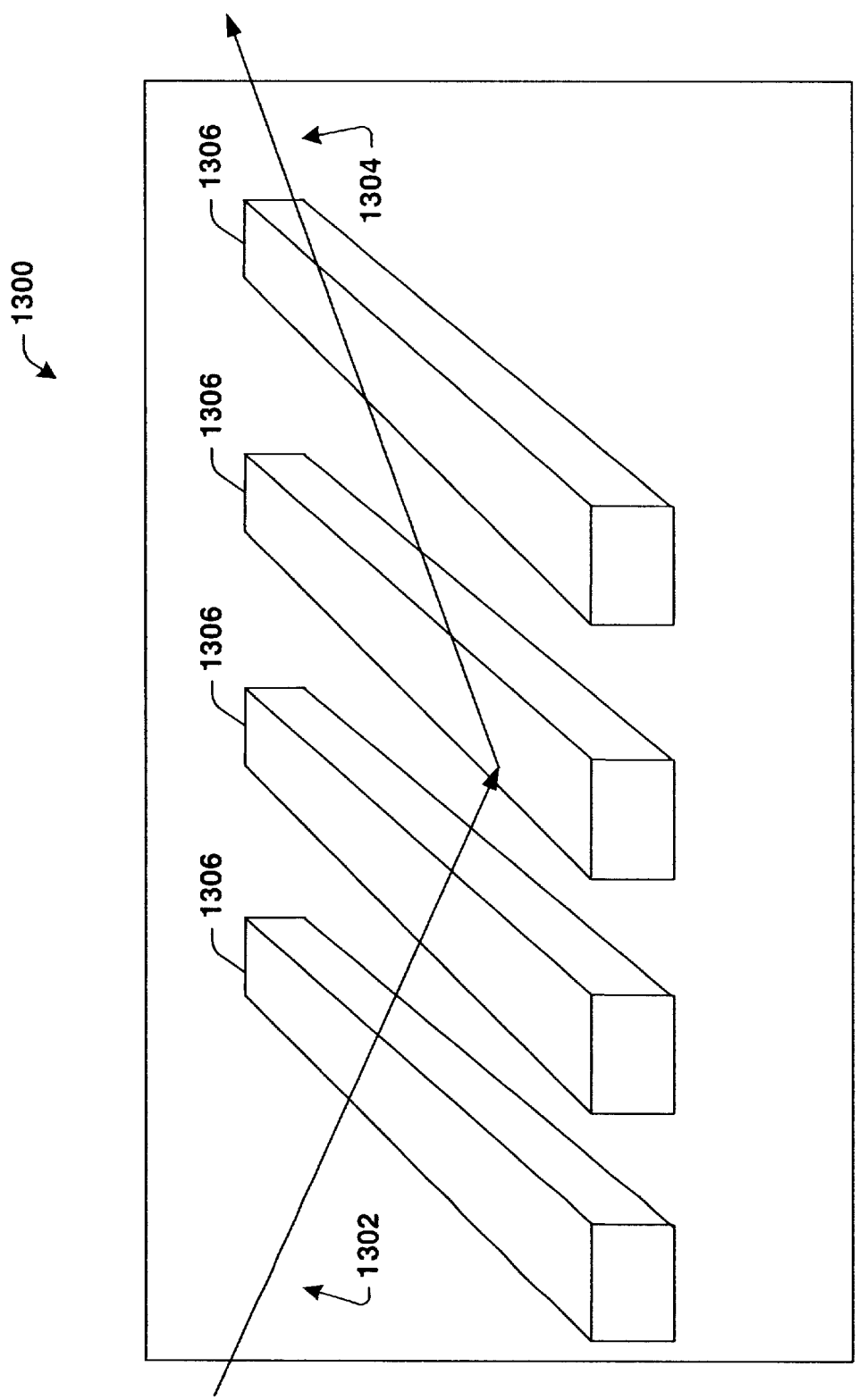
FIG. 9 is a simplified perspective view of an incident light reflecting off a surface, in accordance with an aspect of the present invention.

To illustrate the principles described above, reference is now made to FIGS. 9 through 14. Referring initially to FIG. 9, an incident light 1302 is directed at a surface 1300, upon which one or more features 1306 may exist. The incident light 1302 is reflected as reflected light 1304. The properties of the surface 1300, including but not limited to, thickness, uniformity, planarity, chemical composition and the presence of features, can affect the reflected light 1304. The features 1306 are raised upon the surface 1300. The phase and intensity of the reflected light 1304 can be measured and plotted, as shown, for example, in FIG. 14. Such plots can be employed to compare measured signals with signatures stored in a signature library using techniques like pattern matching, for example.

Figure 10:
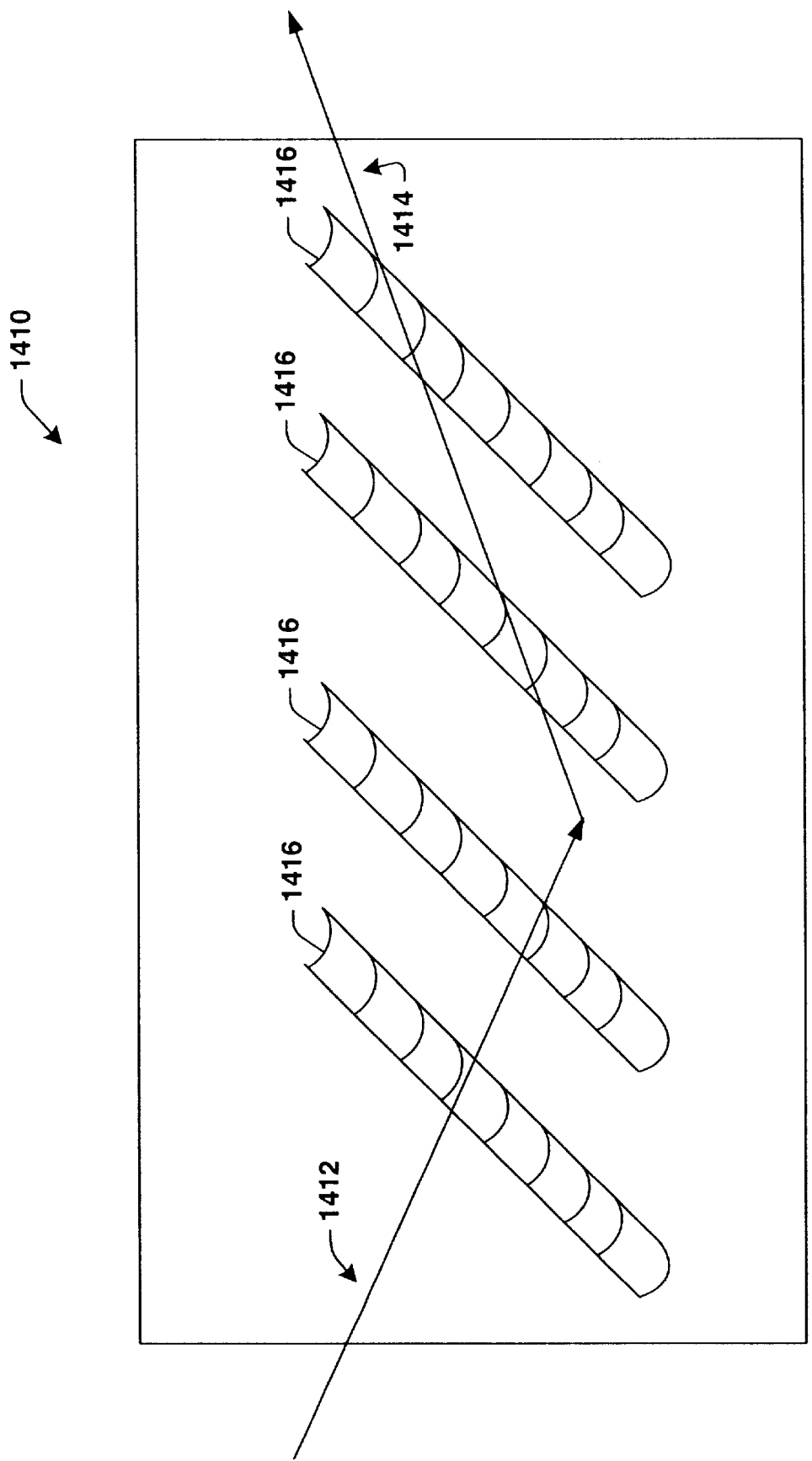
FIG. 10 is a simplified perspective view of an incident light reflecting off a surface, in accordance with an aspect of the present invention.

Referring now to FIG. 10, an incident light 1412 is directed onto a surface 1410 upon which one or more depressions 1416 appear. The incident light 1412 is reflected as reflected light 1414. Like the one or more features 1306 (FIG. 9) may affect an incident beam, so too may the one or more depressions 1416 affect an incident beam. Thus, it is to be appreciated that scatterometry can be employed to measure features appearing on a surface, features appearing in a surface, and properties of a surface itself, regardless of features.

Figure 11:
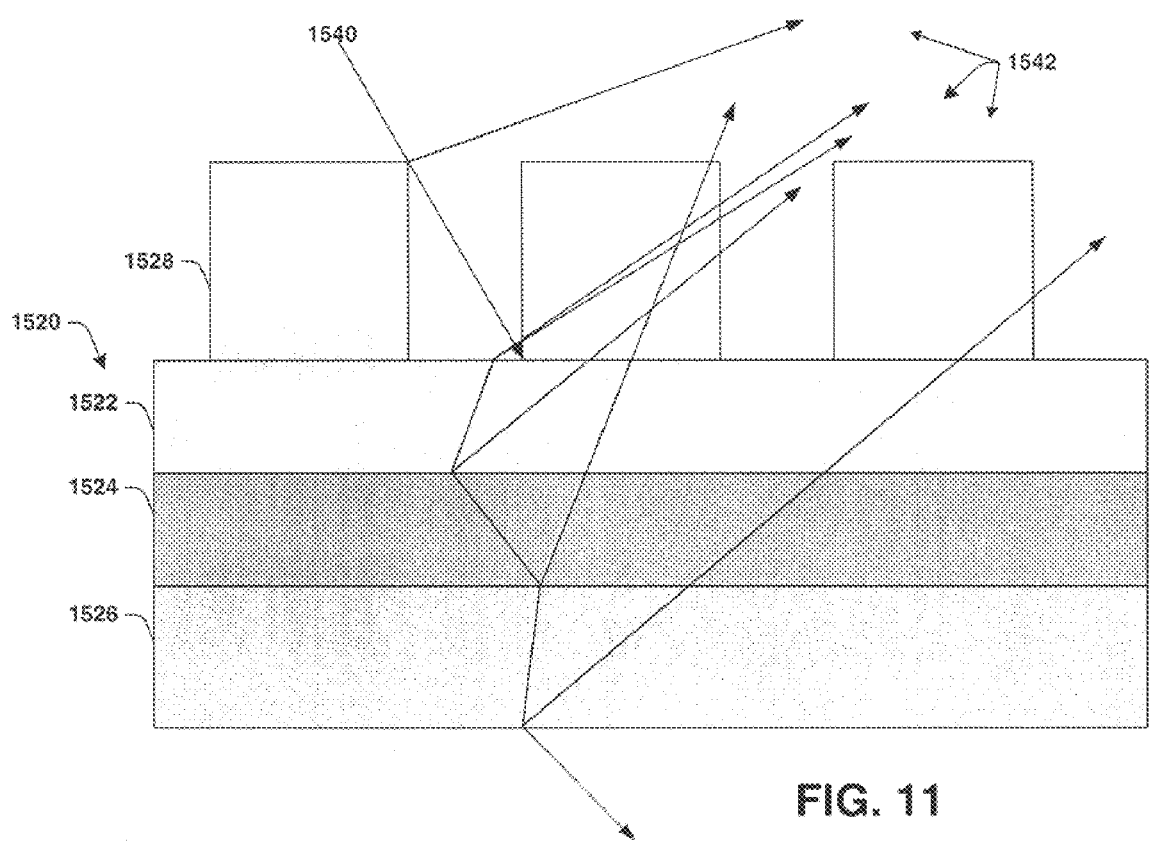
FIG. 11 illustrates a complex reflected and refracted light produced when an incident light is directed onto a surface, in accordance with an aspect of the present invention.

Turning now to FIG. 11, complex reflections and refractions of an incident light 1540 are illustrated. The reflection and refraction of the incident light 1540 can be affected by factors including, but not limited to, the presence of one or more features 1528, and the composition of the substrate 1520 upon which the features 1528 reside. For example, properties of the substrate 1520 including, but not limited to the thickness of a layer 1522, the chemical composition of the layer 1522, the opacity and/or reflectivity of the layer 1522, the thickness of a layer 1524, the chemical composition of the layer 1524, the opacity and/or reflectivity of the layer 1524, the thickness of a layer 1526, the chemical composition of the layer 1526, and the opacity and/or reflectivity of the layer 1526 can affect the reflection and/or refraction of the incident light 1540. Thus, a complex reflected and/or refracted light 1542 may result from the incident light 1540 interacting with the features 1528, and/or the layers 1522, 1524 and 1526. Although three layers 1522, 1524 and 1526 are illustrated, it is to be appreciated that a substrate can be formed of a greater or lesser number of such layers.

Figure 12:
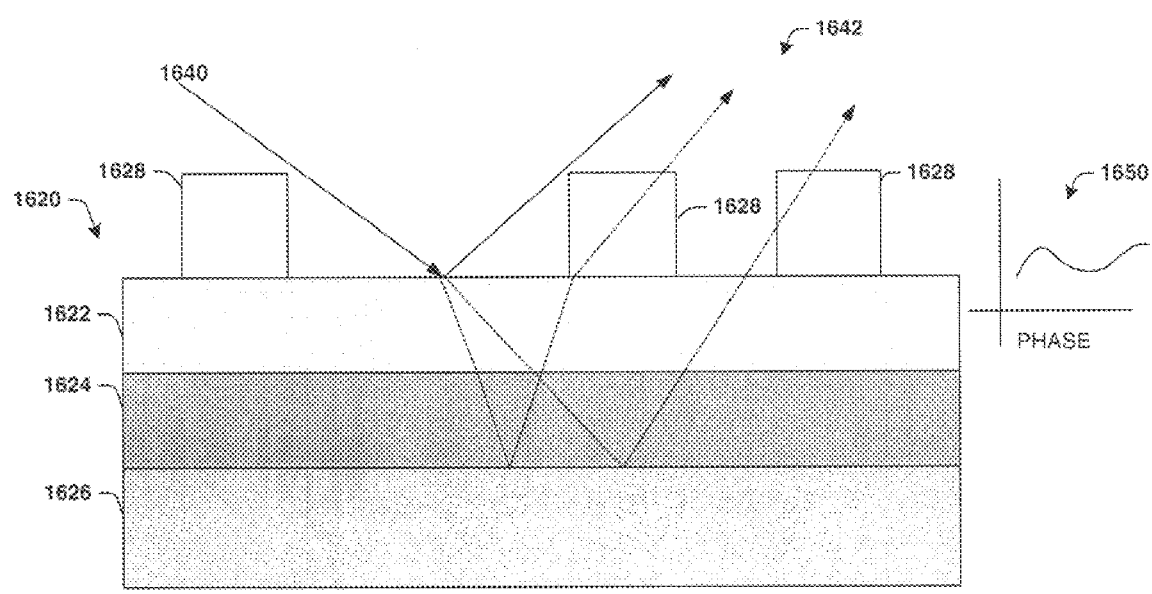
FIG. 12 illustrates a complex reflected and refracted light produced when an incident light is directed onto a surface, in accordance with an aspect of the present invention.
Figure 13:
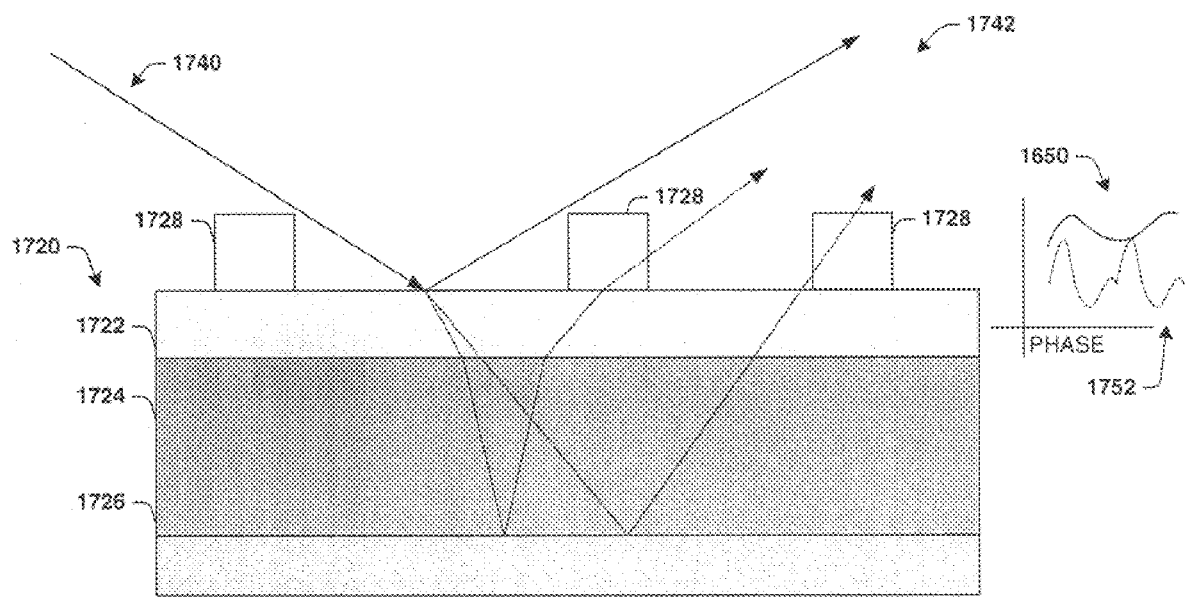
FIG. 13 illustrates a complex reflected and refracted light produced when an incident light is directed onto a surface, in accordance with an aspect of the present invention.
Figure 14:
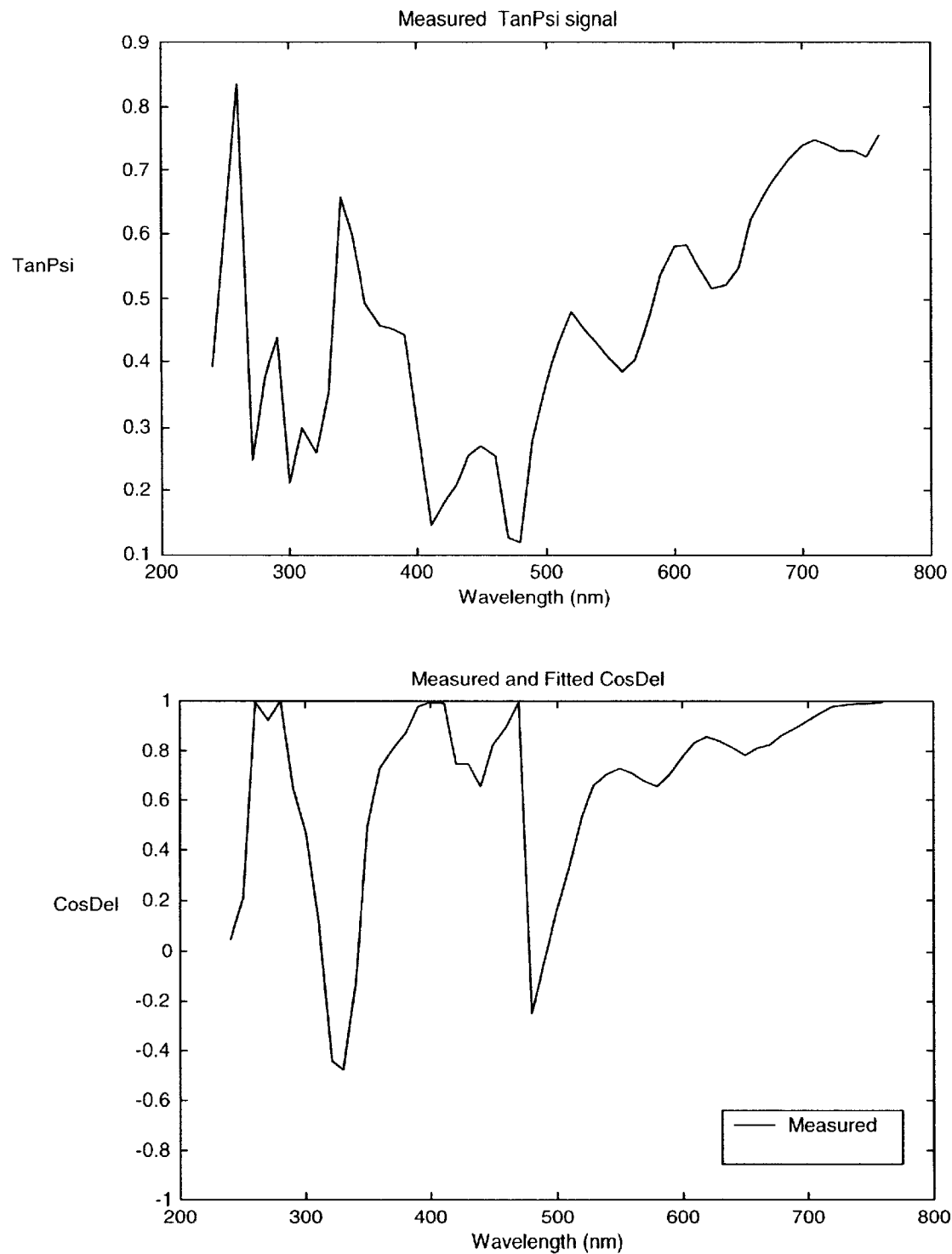
FIG. 14 illustrates phase and intensity signals recorded from a complex reflected and refracted light produced when an incident light is directed onto a surface, in accordance with an aspect of the present invention.

Turning now to FIG. 12, one of the properties from FIG. 13 is illustrated in greater detail. The substrate 1620 can be formed of one or more layers 1622, 1624 and 1626. The phase 1650 of the reflected and/or refracted light 1642 can depend, at least in part, on the thickness of a layer, for example, the layer 1624. Thus, in FIG. 13, the phase 1752 of a reflected light 1742 differs from the phase 1650 due, at least in part, to the different thickness of the layer 1724 in FIG. 13 from the thickness of the layer 1624 in FIG. 12.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

The present invention provides for a system and method for regulating development time. As a result, the present invention facilitates improving development integrity and reliability, which in turn increases quality of image transfer in lithographic processes in accordance with the present invention.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system adapted to provide in-situ detection of closed area defects, comprising:

a light source for directing light on to a wafer having a grating pattern etched thereon;

a light detector for collecting the light reflected from the wafer;

a processor operatively coupled to the light detector for converting the collected light into data associated with the grating pattern and determining the presence of the closed area defect; and a controller operatively coupled to the processor for determining whether the wafer requires additional processing to repair the closed area defect.

2. The system of claim 1, wherein the processor comprises a scatterometry system.

3. The system of claim 1, wherein the light detector collects lights in accordance with a scatterometry system.

4. The system of claim 1, wherein the processor partitions the wafer into a coordinate grid comprising one or more grid blocks and determines the presence of closed area defects at the one or more grid blocks.

5. The system of claim 1, wherein the controller activates an alarm to signal that the wafer requires additional processing to repair the closed area defect.

6. The system of claim 1, wherein the closed area defect comprises at least one of extrusion defects, intrusion defects, corner defects, pinhole defects, or a combination thereof.

7. The system of claim 1, wherein the processor determines the presence of the closed area defect by comparing the data associated with the grating pattern to a database comprising known grating patterns.

8. A system adapted to provide in-situ detection and mitigation of closed area defects, comprising:

one or more grating fabrication components for creating a grating pattern on a wafer;

a light source for directing light on to the wafer having the grating pattern etched thereon;

a light detector for collecting the light reflected from the wafer;

a processor operatively coupled to the light detector for converting the collected light into data associated with the grating pattern and determining the presence of the closed area defect; and a controller operatively coupled to the processor for determining whether the wafer requires additional processing to repair the closed area defect and for communicating adjustments to the one or more grating fabrication components in order to mitigate subsequent occurrences of closed area defects.

9. The system of claim 8, wherein the processor comprises a scatterometry system.

10. The system of claim 8, wherein the light detector collects lights in accordance with a scatterometry system.

11. The system of claim 8, wherein the processor partitions the wafer into a coordinate grid comprising one or more grid blocks and determines the presence of closed area defects at the one or more grid blocks.

12. The system of claim 8, wherein the controller activates an alarm to signal that the wafer requires additional processing to repair the closed area defect.

13. The system of claim 8, wherein the closed area defect comprises at least one of extrusion defects, intrusion defects, corner defects, pinhole defects, or a combination thereof.

14. The system of claim 8, wherein the processor determines the presence of the closed area defect by comparing the data associated with the patterned grating to a database comprising known grating patterns.

15. A method for detection and reduction of closed area defects on a wafer comprising:

directing a light at the wafer having a grating patterned etched thereon;

collecting a light signature reflected from the wafer;

detecting for the presence of the closed area defects on the wafer; and if the closed area defects are detected, then proceeding to additional processing to reduce the closed area defects.

16. The method of claim 15, wherein the light is directed in accordance with a scatterometry system.

17. The method of claim 15, wherein the light signature is collected in accordance with a scatterometry system.

18. The method of claim 15, wherein the wafer is partitioned into a coordinate grid comprising one or more grid blocks and the presence of the closed area defects are detected at the one or more grid blocks.

19. The method of claim 15, wherein signaling the wafer to proceed to additional processing comprises activating an alarm.

20. The method of claim 15, wherein the closed area defect comprises any one of extrusion defects, intrusion defects, corner defects, pinhole defects, or a combination thereof.

21. The method of claim 15, wherein the presence of the closed area defects is determined by comparing the data associated with the grating pattern to a database comprising known grating patterns.

22. A method for detection and reduction of closed area defects on a wafer comprising:

patterning a grating onto the wafer using one or more grating fabrication components;

directing a light at the wafer having the grating patterned etched thereon;

collecting a light signature reflected from the wafer;

detecting for the presence of the closed area defects on the wafer;

if the closed area defects are detected, then performing additional processing to reduce the closed area defects; and if the closed area defects are detected, then communicating determined adjustments to the one or more grating fabrication components.

23. The method of claim 22, wherein the light is directed in accordance with a scatterometry system.

24. The method of claim 22, wherein the light signature is collected in accordance with a scatterometry system.

25. The method of claim 22, wherein the wafer is partitioned into a coordinate grid comprising one or more grid blocks and the presence of the closed area defects are detected at the one or more grid blocks.

26. The method of claim 22, wherein signaling the wafer to proceed to additional processing comprises activating an alarm.

27. The method of claim 22, wherein the closed area defect comprises any one of extrusion defects, intrusion defects, corner defects, pinhole defects, or a combination thereof.

28. The method of claim 22, wherein the presence of the closed area defects is determined by comparing the data associated with the patterned grating to a database comprising known grating patterns.

29. A system for detection and reduction of closed area defects on a wafer comprising:

means for directing a light at the wafer having a grating patterned etched thereon;

means for collecting a light signature reflected from the wafer;

means for detecting for the presence of the closed area defects on the wafer; and means for performing additional processing on the wafer to address the detected closed area defect.

* * * * *